(12) United States Patent
Bertini et al.

(10) Patent No.: US 8,110,676 B2
(45) Date of Patent: Feb. 7, 2012

(54) PRODRUGS ACTIVATED BY RNA-DEPENDENT DNA-POLYMERASES

(75) Inventors: Ivano Bertini, Florence (IT); Claudio Luchinat, Florence (IT); Alessandro Quattrone, Prato (IT); Massimo Calamante, Monsummano Terme (IT); Alessandro Mordini, Florence (IT)

(73) Assignee: Protera S.R.L., Sesto Fiorentino (IT)

( * ) Notice: Subject to any disclaimer, the term of this patent is extended or adjusted under 35 U.S.C. 154(b) by 600 days.

(21) Appl. No.: 11/659,269

(22) PCT Filed: Aug. 2, 2005

(86) PCT No.: PCT/EP2005/053765
§ 371 (c)(1),
(2), (4) Date: Feb. 2, 2007

(87) PCT Pub. No.: WO2006/013203
PCT Pub. Date: Feb. 9, 2006

(65) Prior Publication Data
US 2008/0300215 A1    Dec. 4, 2008

(30) Foreign Application Priority Data
Aug. 3, 2004   (IT) ................ FI2004A0173

(51) Int. Cl.
*C07H 19/20*    (2006.01)

(52) U.S. Cl. .................... 536/26.22; 536/26.26
(58) Field of Classification Search .................. None
See application file for complete search history.

(56) References Cited

FOREIGN PATENT DOCUMENTS

| GB | 2 168 353 | 6/1986 |
|---|---|---|
| WO | WO 03/072757 | 9/2003 |
| WO | WO 2004/064782 | 8/2004 |

OTHER PUBLICATIONS (R) Cai et al.. "Quantitative Assessment of mRNA Cap Analogues as Inhibitors of in Vitro Translation," Biochemistry, 38(26), 8538-8547 (1999); Web Publ. on Jun. 11, 1999.*
(S) Bisacchi et al., "BMS-200475, A Novel Carbocyclic 2'-Deoxyguanosine Analog with Potent and Selective Anti-Hepatitis B Virus Activity in vitro," Bioorganic & Medicinal Chemistry Letters, 7(2), 127-132 (1997).*
Tomoyuki et al., "Nucleotide Dimer," Patent Abstracts of Japan, from JP 09 020792 Abstract, 1997.
International Search Report from WO 2006/013203 A3, (Feb. 2, 2006).

* cited by examiner

*Primary Examiner* — Lawrence E Crane
(74) *Attorney, Agent, or Firm* — Clark & Elbing LLP

(57) ABSTRACT

The invention provides prodrugs activated by RNA-dependent DNA-polymerases, and methods for treating hematological tumors, blood, and blood derivatives from patients affected by retroviral infections by administering the prodrugs. The invention also provides methods for the preparation of pharmaceutical compositions containing the prodrugs.

8 Claims, No Drawings

PRODRUGS ACTIVATED BY RNA-DEPENDENT DNA-POLYMERASES

CROSS-REFERENCE TO RELATED APPLICATIONS

This application claims priority under 35 U.S.C. §371 from international application PCT/EP2005/053765, filed Aug. 2, 2005, which claims priority from Italian Application No. FI2004A000173, filed Aug. 3, 2004.

FIELD OF INVENTION

The present invention relates to the field of compounds useful as prodrugs, and in particular prodrugs activated in cancer cells and in cells infected by retroviruses, by DNA-polymerising enzymes, which use a RNA molecule as template, such as human telomerase and HIV reverse transcriptase.

STATE OF ART

At present the therapeutic treatment of cancer and retrovirus-caused pathologies is strongly limited in its effectiveness due to the low selectivity of the drugs used for cancer cells and for retrovirally infected cells. Both neoplastic transformation and retroviral infection do not transform cells in such a way that after phenotypic change they can easily become a selective target for drugs. Cancer pharmacology, for example, is still based on cytotoxic drugs that are highly harmful also for the healthy cells of the individual, while anti-AIDS drugs have serious side effects mostly due to their interference with the normal physiology of non-infected cells.

This lack of selectivity of anticancer and antiretroviral drugs is the cause of their high toxicity in vivo. Moreover in the case of cancer such unwanted secondary effects are not compensated by a long-lasting satisfying remission, especially in cases of advanced solid tumours, which still represent an incurable disease with survival chances tending, in the long term, to zero. It would therefore be good to have more selective antiretroviral and anticancer agents, both to minimise the side effects and to increase their effectiveness and therapeutic index.

In recent years attempts have been made to administrate cytotoxic drugs as "prodrugs". From a therapeutic point of view "prodrug" is an inactive compound, which can be transformed in vivo into an active drug, i.e. into a compound therapeutically active, thanks to chemical or enzymatic transformations of its structure.

The difficulty in providing a good prodrug does not only lie in finding a molecule able to activate in vivo, but also in making this activation highly selective for the target cells. In other words, the ideal candidate anticancer or antiretroviral prodrug is that activating into drug, exerting thereby a cytotoxic action that kills the infected or cancer cells only after having reached them, remaining stable and inactive in the healthy tissues.

This makes it felt the need to develop anticancer and antiretroviral prodrugs.

SUMMARY OF THE INVENTION

Now the Applicant has developed novel anticancer and antiretroviral prodrugs, wherein an active cytotoxic compound is incorporated into a molecule which is hydrolysable from RNA-dependent DNA-polymerases, such as telomerase or retroviral reverse transcriptases, releasing by hydrolysis a cytotoxic fragment or a fragment precursor of a cytotoxic compound.

Subject of the present invention is therefore a prodrug compound comprising a moiety hydrolysable by RNA-dependent DNA polymerases covalently bound to a residue of a cytotoxic compound or of a precursor of a cytotoxic compound, wherein the hydrolysis product of said prodrug compound is cytotoxic, and pharmaceutically acceptable salts thereof.

Further subject of the invention are the process for preparing the above said prodrug compound, the pharmaceutical compositions comprising at least a compound as defined above, optionally in association with one or more adjuvants and/or other active principles, as well as the use of the above said compounds for preparing pharmaceutical compositions useful for the treatment of solid tumours, of precancerous states and of diseases caused by infection with retroviruses.

Further subject of the invention are agents for the ex vivo or in vivo treatment of haematological tumours and for the treatment of blood and blood derivatives taken from patients affected by retroviral infections, comprising at least a prodrug compound as defined above; the use of the prodrug compounds as defined above, for the ex vivo treatment of haematological tumours and for the treatment of blood and blood derivatives from patients affected by retroviral infections; the method for treating ex vivo or in vivo haematological tumours and blood and blood derivatives taken from patients affected by retroviral infections comprising the step of contacting blood or blood derivatives to be treated with at least a compound as defined above; a method for increasing the effectiveness and tolerability of a cytotoxic compound comprising the formation of a prodrug wherein said cytotoxic compound is bound to a moiety hydrolysable by RNA-dependent DNA polymerases; and a therapeutic method for the treatment of solid tumours, of precancerous states and of diseases caused by infection with retroviruses, comprising administering to a patient in need of such a treatment a pharmaceutically effective amount of at least a compound as defined above, optionally in association with one or more adjuvants and/or other active principles. Features and advantages of the compounds of the invention will be described in detail in the following description.

DETAILED DESCRIPTION OF THE INVENTION

According to the present invention by the expression "the hydrolysis product of said prodrug compound is cytotoxic" it is meant that the hydrolysis product may be a cytotoxic fragment as such or it is a fragment that may become cytotoxic following chemical transformations by cells activities. By the term "fragment" a portion of the prodrug compound, which is liberated by hydrolysis, is meant.

Telomerase is a RNA-dependent DNA-polymerase which adds nucleotides to the ends of the telomeres, the extremities of chromosomes. Due to its enzymatic activity it is similar to the reverse transcriptases of retroviruses; the difference from the above said other enzymes is that telomerase is a ribonucleoprotein, being the RNA template incorporated in the complex.

Most of somatic human cells do not reveal telomerase activity; therefore telomeres undergo progressive shortening during successive cellular divisions until telomeres reach a critical minimal length signal to the cell replicative block and entry in the so called senescent state. On the contrary, in most of cancer cells telomerase activity is restored, therefore telomere length is maintained constant and transformed cells can proliferate limitless, allowing expansion of the cancer clone and subserving metastatic spread. Research in this field brought to the development of compounds proposed as antitumour agents that inhibit telomerase activity. Nevertheless, attempts to demonstrate the anticancer action of these compounds showed that even when the compounds were effective in blocking telomerase activity the time necessary for telomere shortening to the critical length was too long to effectively contrast cancer progression.

The Applicant has exploited telomerase activity, typical of cancer cells, in a reversed perspective. Instead of trying to inhibit it, the Applicant has designed and produced prodrugs which are activated to cytotoxic compounds by the telomerase enzymes themselves; in this case the therapeutic efficiency is not function of enzyme inhibition but function of its activity, which specifically releases cytotoxic compounds only within the target cells, where telomerase is present.

The same molecules are also recognised by retroviral reverse transcriptases, such as the HIV-1 reverse transcriptase, etiological cause of AIDS, due to the common enzymatic mechanism of all RNA-dependent DNA-polymerases, and are therefore useful also for the treatment of diseases caused by retroviral infection, such as AIDS. According to the present invention the prodrug compound, consisting for example of an analogue of a dinucleotide polyphosphate, is recognised as substrate, and the hydrolysis catalysed by telomerase or retroviral reverse transcriptases is obtained, with the consequent releasing of the cytotoxic molecule.

The hydrolysable moiety of the compounds of the invention preferably comprises a portion, which is substrate of RNA-dependent DNA-polymerases, bound covalently to a chain comprising at least three groups, identical or different from each other, selected from phosphate, phosphonate, thiophosphate or thiophosphonate, possibly substituted with one or more further residues of cytotoxic compounds, identical or different from the first residue, or with one or more R groups selected from the group consisting of alkyl, in particular lower alkyl, aryl and aryl alkyl.

Preferred compounds according to the invention are compounds having general formula (I)

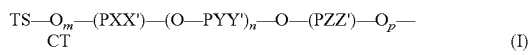

wherein

TS is a portion recognised by the catalytic site of a RNA-dependent DNA polymerases, CT is a residue of a cytotoxic compound or of a precursor of a cytotoxic compound, X, Y, and Z are chosen from between O and S, X', Y' and Z' are chosen from amongst O, CT', O-CT', R and OR, wherein CT' is a residue of a cytotoxic compound or of a precursor of a cytotoxic compound equal or different from CT, and R is selected from the group consisting of alkyl, in particular lower alkyl, aryl and aryl alkyl, m=0, 1; n=1, 2; p=0, 1.

More preferred compounds are the compounds of formula (I) wherein X=X'=Z=Z'=O, and m=1.

When not otherwise specified, the terms "alkyl", "lower alkyl", "aryl" and "alkyl aryl", as used in this invention, should be understood as follows:

the term "alkyl" refers to hydrocarbon chains, linear or branched, only having simple bonds, and preferably to a C1-C20 chain. Examples of alkyl groups according to the invention include, but are not limited to, methyl, ethyl, propyl, iso-propyl, n-butyl, iso-butyl, tertbutyl, pentyl, isopentyl, neopentyl, and tert-pentyl.

the term "lower alkyl" refers to an alkyl, linear or branched, having from 1 to 7 carbon atoms in the chain, preferably from 1 to 4 carbon atoms. Examples of lower alkyl groups according to the invention include, but are not limited to, methyl, ethyl, propyl, iso-propyl and n-butyl.

the term "aryl" refers to carbocycle or heterocycle groups comprising one or more unsaturated rings, each ring having from 5 to 8 members, and preferably 5 or 6 members. Examples of aryl groups according to the invention include, but are not limited to, phenyl, pyridyl, tolyl, naphtyl, antracenyl, and phenantryl.

the term "aryl alkyl" refers to a group having an alkyl substituent and an aryl substituent as above defined. Examples of alkyl aryl according to the invention include, but are not limited to, ethylbenzenyl, isobutylbenzenyl, benzyl, ethylbenzyl, propylbenzyl, isopropylbenzyl, butylbenzyl, isobutylbenzyl, cycloesylbenzyl, stirenyl and biphenyl.

According to the invention, the groups alkyl, lower alkyl, aryl and aryl alkyl, can possibly be substituted, for example by groups OH, $NH_2$, halides and with hydrocarbon chains having at least a double or triple bond, such as C2-8 alkenyl and C2-8 alkynyl groups. The group R is preferably chosen from between methyl and phenyl, and it is more preferably phenyl.

The Applicant found that the substituents bound to the hydrolysable moiety do not cancel, despite the steric hindrance, the hydrolytic activity in extracts of cancer cells cultures, allowing the molecule bound to the telomerase substrate to be freed. According to a preferred embodiment of the invention, the portion TS is the residue of a nucleoside or an analogue thereof, selected for example from the group consisting of deoxyguanosine, deoxyadenosine, deoxythymidine, 7-deaza- 2'-deoxyguanosine, 7-deaza-2'adenosine, 6-thio-2'-deoxyguanosine, 2', 3'- dideoxyguanosine, 2',3'-dideoxyinosine, D-carbocycle-2'-deoxyguanosine, azidothymidine, carbovir, adefovir and tenofovir.

The activation of the prodrug by RNA-dependent DNA polymerases occurs by hydrolysis of a P—O bond, with the release of the cytotoxic compound or a precursor thereof.

Cytotoxic compounds that could possibly be used for the preparation of the present prodrugs are selected from the group consisting of acyclovir, penciclovir, ganciclovir, 7-methyl-guanosine, gemcitabine, fluorodeoxyuridine, fluorouridine, fludarabine, 2-chlorodeoxyadenosine, idoxuridine, cytarabine, triciribine, 5-aza-2'deoxycytidine, 2'3'-didehydrouridine-2'3'-deoxyuridine, 5-hydroxy-2'-deoxycytidine, 3-deazauridine, enocitabine, 2',3'-dideoxycytidine, lamivudine, emtricitabine, (S)-1-(3-hydroxy-1-methoxypropyl)cytosine, (−)-2'-deoxy-3'-oxa-4'-thiocytidine, racivir, reverset, 1-(1,3-dihydroxy-2-propoxymethyl)cytosine, (2'S)-2'-deoxy-2'-C-methylcytidine, 1-(2-deoxy-2-methylene-β-D-erithro-pentofuranosyl)cytosine, 1-(2-C-cyano-2-deoxy-1-β-D-arabino-pentofuranosyl) cytosine, 1-(3-C-ethynyl-β-D-ribo-pentofuranosyl)cytosine, β-L-dioxolane-cytidine, and (E)-2'-deoxy-2'-(fluoromethylene)cytidine.

The above said preferred portions TS are bound to the chain of the phosphate, phosphonate, thiophosphate or thiophosphonate groups in the position indicated by an asterisk in the following formulas representing the corresponding nucleosides or analogues thereof:

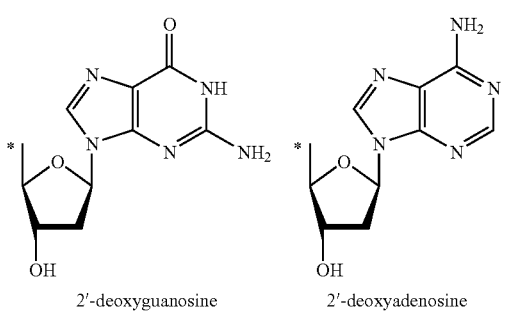

2'-deoxyguanosine

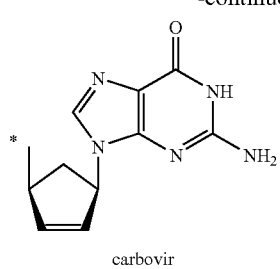

2'-deoxyadenosine

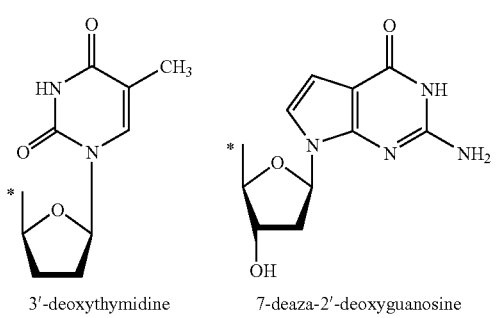

3'-deoxythymidine 7-deaza-2'-deoxyguanosine

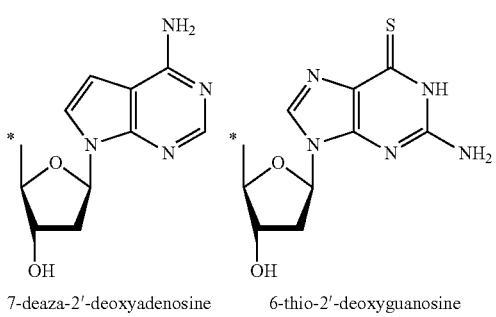

7-deaza-2'-deoxyadenosine 6-thio-2'-deoxyguanosine

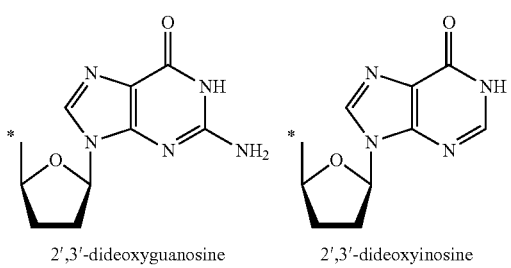

2',3'-dideoxyguanosine 2',3'-dideoxyinosine

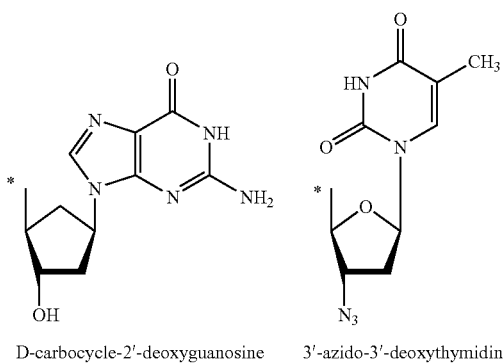

D-carbocycle-2'-deoxyguanosine 3'-azido-3'-deoxythymidine

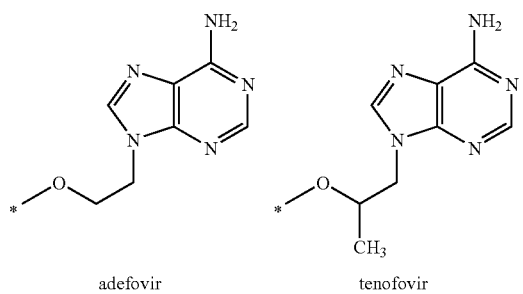

carbovir adefovir tenofovir

Preferred residues CT or CT', as listed above, are bound to the chain of phosphate, phosphonate, thiophosphate or thiophosphonate groups in the position indicated by an asterisk in the following formulas representing the corresponding cytotoxic compounds:

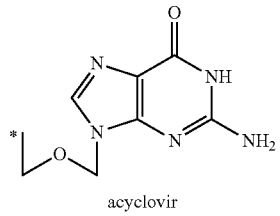

acyclovir

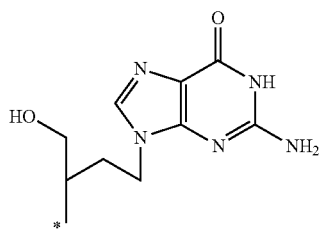

penciclovir

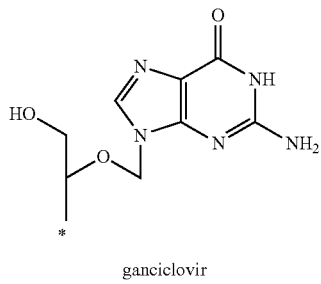

ganciclovir

-continued

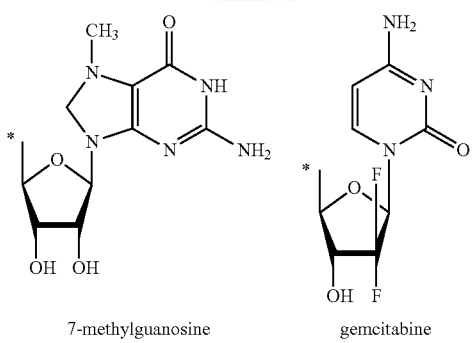

7-methylguanosine
gemcitabine

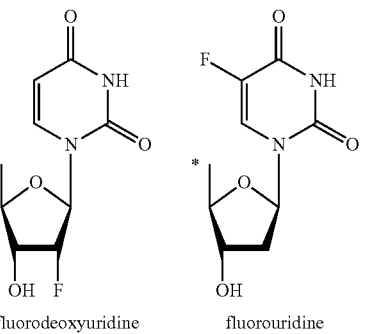

fluorodeoxyuridine
fluorouridine

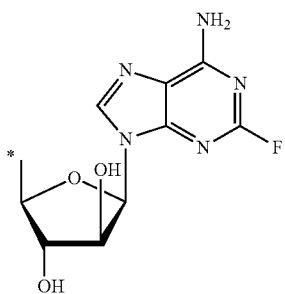

fludarabine

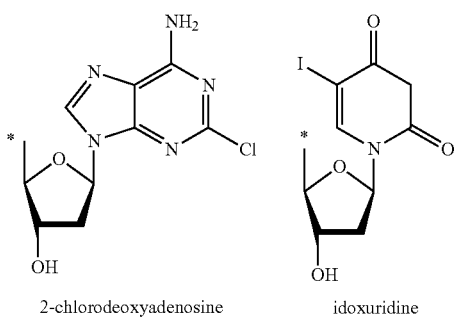

2-chlorodeoxyadenosine
idoxuridine

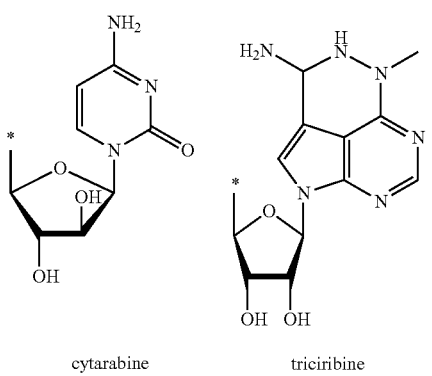

cytarabine
triciribine

-continued

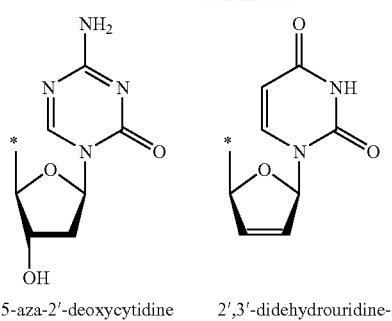

5-aza-2′-deoxycytidine
2′,3′-didehydrouridine-2′,3′-deoxyuridine

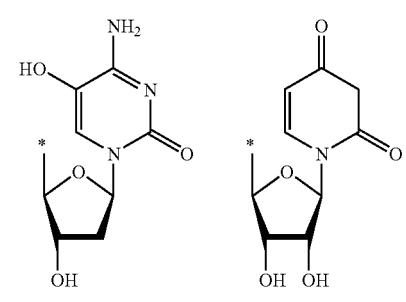

5-hydroxy-2′-deoxycytidine
3-deazauridine

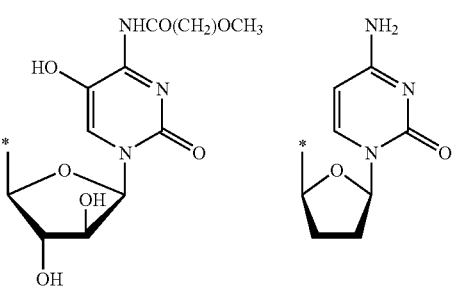

enocitabine
2′,3′-dideoxycytidine

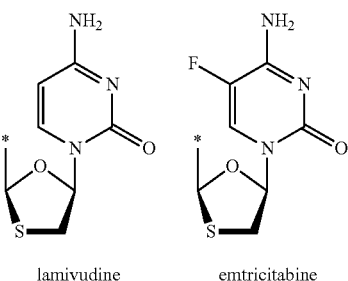

lamivudine
emtricitabine

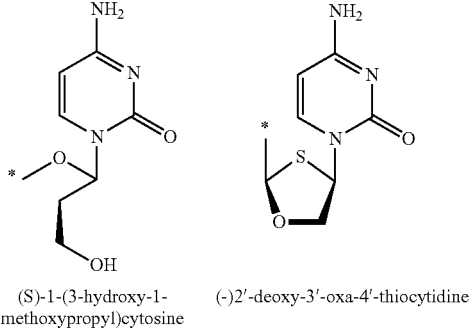

(S)-1-(3-hydroxy-1-methoxypropyl)cytosine
(−)2′-deoxy-3′-oxa-4′-thiocytidine

-continued

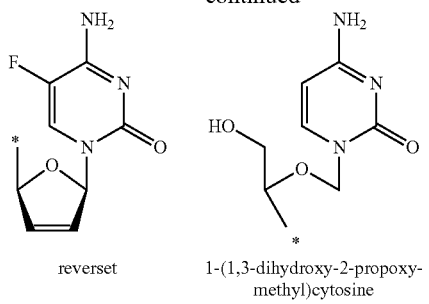

reverset     1-(1,3-dihydroxy-2-propoxy-methyl)cytosine

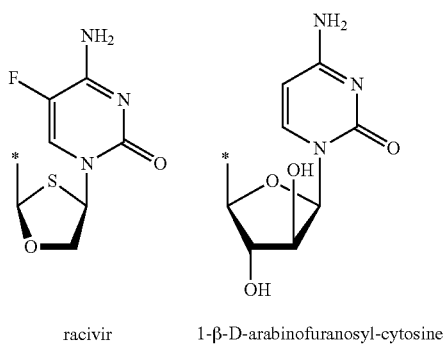

racivir     1-β-D-arabinofuranosyl-cytosine

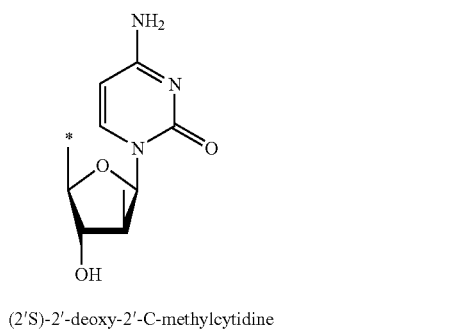

(2'S)-2'-deoxy-2'-C-methylcytidine

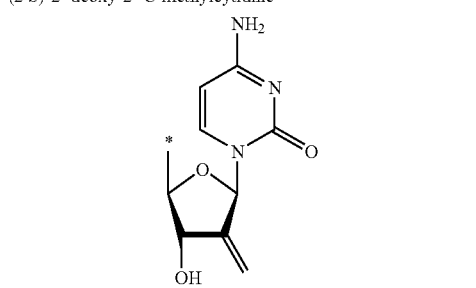

1-(2-deoxy-2-methylene-β-D-erythro-pentofuranosyl)cytosine

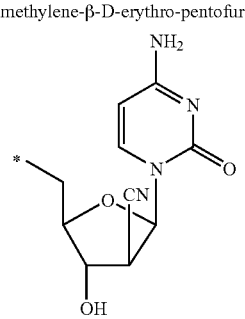

1-(2-C-cyano-2-deoxy-1-β-D-arabino-pentofuranosyl)cytosine

-continued

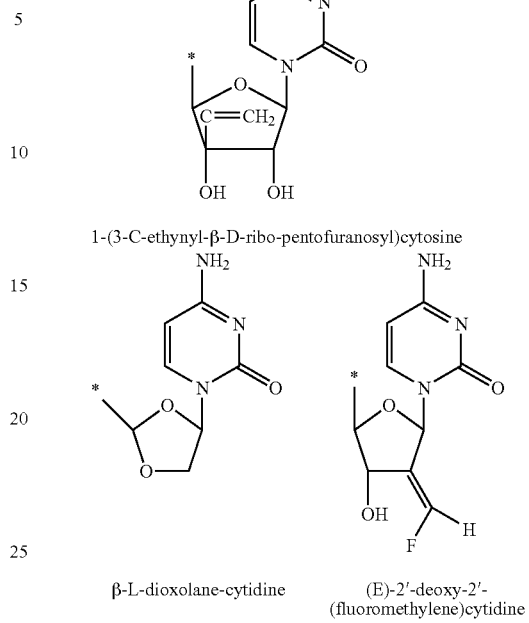

1-(3-C-ethynyl-β-D-ribo-pentofuranosyl)cytosine

β-L-dioxolane-cytidine     (E)-2'-deoxy-2'-(fluoromethylene)cytidine

The present compounds, in free form or in the form of pharmaceutically acceptable salts, can be used for the preparation of pharmaceutical compositions according to the conventional methods of preparation of pharmaceutical compositions, and may comprise one or more pharmaceutically acceptable excipients and/or diluents.

Administration of the present pharmaceutical compositions may be achieved in any conventional way, for example parenteral, oral, topical, nasal, etc., in particular by parenteral, intravenous, intramuscular or intraperitoneal administration. Therefore, formulations of the compounds according to the invention include in particular sterile aqueous and not aqueous solutions, suspensions, emulsions and sterile solid compositions to be dissolved in a sterile medium at the moment of use, and they may further comprise pharmaceutically acceptable excipients and/or diluents.

The present pharmaceutical compositions can comprise at least one of the present compounds as active principle, possibly in association with other suitably selected adjuvants and/or active principles, in particular antimetabolites, such as methotrexate, 5-fluorouracil, citarabine, 5-azacytidine, gemcitabine, mercaptopurine, tioguanine, fludarabine phosphate, pentostatine and cladribine.

The prodrugs of the invention are useful for the treatment of solid tumours, of precancerous states and of diseases caused by infection with retrovirus; moreover they can be used for the treatment in vivo and ex vivo of haematological tumours and for purification of blood and derivatives of blood taken from patients infected with retroviruses.

Administration of the present prodrugs may be carried out also in association with one or more further active principles, in particular antimetabolites, such as those mentioned above, comprised in the same pharmaceutical composition as the present prodrugs or in another pharmaceutical composition to be administered with the present one in a combined chemotherapy protocol.

The compounds described above may be prepared starting from the cytotoxic compound, which in suitable conditions and by known methods, are covalently bound to an appropriate chain consisting of at least three groups of phosphate, phosphonate, tiophosphate or tiophosphonate and are therefore, through this chain, bound to a part of the molecule recognisable as substrate by telomerase or reverse transcriptases, or vice versa.

All starting compounds for the preparation of the present compounds are products available on the market, or may be prepared by processes known to any person skilled in the field starting from products available on the market.

The following examples are reported for not limiting illustration of the present invention.

EXAMPLE 1

Preparation of Acyclovir Monophosphate (ACVMP)

ACVMP was prepared using a procedure adapted from Yoshikawa et al. *Tetrahedron Lett.* 1967, 50, 5065. A mixture of 1 g acyclovir (4.3 mmol) and 6 ml triethylphosphate was gradually added to a mixture of 4 ml triethylphosphate and 860 μl phosphorus oxychloride (8.6 mmol) at 0° C. The mixture was maintained at 0-4° C. for 12 h under stirring. Then 100 ml of diethyl ether were added to precipitate the acyclovir-5'-phosphorodichloridate.

The precipitate was filtered and dissolved in 25 ml of ice-cold 5% $NaHCO_3$ in water. After stirring at 0° C. for 1 h and at room temperature for 8 h, the pH was adjusted to 7.0 with NaOH 1M. After further 12 h under stirring, the mixture was evaporated to dryness, dissolved in the minimum volume of water and loaded onto a DEAE-cellulose column. The column was eluted with a linear gradient (0.05-0.8 M) of triethylammonium bicarbonate, pH 7.5. Appropriate fractions were evaporated under vacuum. Ethanol was added and evaporated again to remove triethylammonium bicarbonate obtaining ACVMP as triethylammonium salt (1.28 g, 2.53 mmol, yield=59%).

$^1$H-NMR ($D_2O$, pH 7.5, 200 MHz) δ (ppm): 1.17-1.21 (t, J=7.3, 18H), 3.06-3.17 (q, J=7.3, 12H), 3.69-3.77 (m, 2H), 3.85-3.94 (m, 2H), 5.51(s, 1H), 7.93 (s, 1H).

$^{31}$P-NMR ($D_2O$, pH 7.5, 80 MHz) δ (ppm): 3.79 (s).

EXAMPLE 2

Preparation of Acyclovir Diphosphate (ACVDP)

ACVDP was synthesised using a procedure adapted from Hoard D. E. et al. *J. Am. Chem. Soc.* 1965, 87, 1785-1788. The tributylammonium orthophosphate, necessary for this transformation, was prepared as follows. Anhydrous orthophosphoric acid (5 g, 51 mmol) and 10 ml of $CH_2Cl_2$ were put in a Schlenk tube, under anhydrous condition. Tributylamine (12.25 ml, 51 mmol) was then added dropwise into the solution in 30 minutes. The mixture was left under stirring for 1 h. $CH_2Cl_2$ was evaporated and the reaction residue re-evaporated with 3×10 ml anhydrous pyridine and 2×10 ml of anhydrous DMF. The final product was dissolved in anhydrous DMF to a concentration of 1M, and stored over molecular sieves (4 Å) at 4° C.

ACVMP triethylammonium salt (1.01 g, 2 mmol) was converted into its pyridinium salt using Dowex 50W-X8 (pyridinium form resin). The column was eluted with 50% aqueous methanol. The eluted was evaporated under reduced pressure to dryness, and then 10 ml methanol and 1.44 ml tributylamine (6 mmol) were added. After 30 minutes stirring, the solution was concentrated under vacuum. The residue was dried by repeated addition and evaporation of anhydrous pyridine (3×10 ml), anhydrous toluene (2×10 ml) and anhydrous DMF (3×10 ml). The resulting ACVMP tributylammonium salt was dissolved in 15 ml anhydrous DMF.

1,1'-Carbonyldiimidazole (1.5 g, 12 mmol) was dissolved in 5 ml DMF. This solution was added to the solution of ACVMP. The mixture was stirred at room temperature on molecular sieve. After 12 hours, 700 μl anhydrous methanol (12 mmol), and after further 30 minutes, 13 ml 1M tributylammonium orthophosphate in DMF (13 mmol) were added dropwise under stirring. After 12 h at room temperature, the precipitate was removed by centrifugation. The supernatant solution was added with 75 ml water and the resulting solution was extract with 3×50 ml $CHCl_3$, subjected to a reduction of volume (5 ml) and loaded on to a DEAE-cellulose column. The column was eluted with linear gradient of triethylammonim bicarbonate (0.05-1M). Appropriate fractions were evaporated under vacuum The residual bicarbonate was eliminated by two sequential evaporation steps from 20 ml methanol. Evaporation to dryness yielded 984 mg ACVDP triethylammonium salt (1.42 mmol, yield=70%).

$^1$H-NMR ($D_2O$, pH 8.5, 200 MHz) δ (ppm): 1.23-1.30 (t, J=7.3, 27H), 3.14-3.25 (q, J=7.3, 18H), 3.77-3.81 (m, 2H), 4.04-4.12 (m, 2H), 5.56 (s, 1H), 7.98 (s, 1H).

$^{31}$P-NMR ($D_2O$, pH 8.5, 80 MHZ) δ (ppm): −6.35:-6.62 (d, J=22.1), −10.62:-10.90 (d, J=22.1).

EXAMPLE 3

Preparation of Acycloguanosyl 2'-deoxy-5'-guanosyltriphosphate (ACVTPdG)

The tributylammonium salt of dGMP and ACVDP were prepared by first converting their sodium salt or triethylammonium salt in pyridinium salt by chromatography on a Dowex 50W-X8 column.

A solution of water (5 ml) and 700 mg dGMP (2 mmol) was loaded onto a Dowex 50W-X8 (pyridinium form). The column was eluted with 50% aqueous methanol. The eluent was evaporated under reduced pressure to dryness, and then 500 μl of tributylamine (2 mmol) and 10 ml water were added. After 30 minutes the mixture was evaporated to dryness. The resulting residue was subjected to 3×10 ml evaporation from anhydrous pyridine and 2×5ml evaporation from anhydrous DMF.

984 mg ACVDP triethylammonium salt (1.42 mmol) was dissolved in 5 ml water loaded on a Dowex 50W-X8 column and eluted with 50% aqueous methanol. The solution was concentrated under vacuum, and then 710 μl tributylamine (2.8 mmol) and 15 ml water were added. After 30 minutes under stirring the reaction mixture was evaporate to dryness, the residue was dried by repeated addition and evaporation of anhydrous pyridine (3×10 ml) and anhydrous DMF (2×10 ml). The anhydrous tributylammonium salt of ACVDP, 14 ml DMF and 910 mg 1,1'-carbonyldiimidazole (7.1 mmol) were mixed in a Schlenk tube under anhydrous conditions. After 12 h stirring at room temperature on molecular sieves, 570 μl methanol (10 mmol) and 30 minutes later the anhydrous tributylammonium salt of dGMP in 6 ml of DMF were added. After additional 14 h stirring, the reaction mixture was evaporated to dryness, dissolved in minimal volume of water and loaded on DEAE-cellulose column. The column was eluted with linear gradient (0.05-1M) of triethylammonium bicarbonate buffer (pH 7.5). ACVTPdG-containing fractions were pooled and concentrated to dryness. The residual bicarbonate was eliminated by two sequential evaporations from 20 ml methanol, and the residual material was converted into its sodium salt using Dowex 50W-X8 resin, after converting the latter from its $H^+$ form to its sodium form by washing with four bed volumes of NaOH 1M, then washing with water until pH neutrality. The resulting preparation was dried under vacuum to a dry yellow powder (350 mg, 0.45 mmol, yield=32%).

$^1$H-NMR (D$_2$O, pH 7.5, 200 MHz) δ (ppm): 2.35-2.48 (m, 1H), 2.65-2.79 (m, 1H), 3.70-3.74 (m, 2H), 4.05-4.20 (m, 5H), 4.65-4.71 (m, 1H), 5.39 (s, 1H), 6.16-6.23 (t, J=6.59, 1H) 7.84 (s, 1H), 7.99 (s, 1H).

$^{31}$P-NMR (D$_2$O, pH 7.5, 80 MHz) δ (ppm): −11.13:−11.37 (d, J=19.53), −11.28:−11.51 (d, J=19.53), −22.90:−23.36 (t, J=19.53).

EXAMPLE 4

Preparation of Acycloguanosyl 2'-deoxy-5'-adenosyltriphosphate (ACVTPdA)

The procedure described above in Example 3 was followed for the preparation of ACVTPdA using 2'-deoxyadenosine-5'-monophosphate disodium salt (dAMP, 165 mg, 0.5 mmol) instead of dGMP and ACVDP tributylammonium salt (194 mg, 0.28 mmol), to give ACVTPdA sodium salt as yellow powder (82 mg, 0.11 mmol, yield=39%).

$^1$H-NMR (D$_2$O, pH 7.5, 200 MHz) δ (ppm): 2.42-2.53 (m, 1H), 2.62-2.75 (m, 1H), 3.61-3.65 (m, 2H), 3.97-4.19 (m, 5H), 4.64-4.71 (m, 1H), 5.29 (s, 1H), 6.31-6.38 (t, J=6.59, 1H) 7.70 (s, 1H), 8.05 (s, 1H), 8.34 (s, 1H).

$^{31}$P-NMR (D$_2$O, pH 7.5, 80 MHz) δ (ppm): −11.41:−11.65 (d, J=19.53), −11.59:−11.83 (d, J=19.53), −23.27:−23.76 (t, J=19.53).

EXAMPLE 5

Preparation of Acycloguanosyl 5'-thymidyltriphosphate (ACVTPT)

The procedure described above in Example 3 was followed for the preparation of ACVTP-T using thymidine-5'-monophosphate disodium salt (TMP, 183 mg, 0.5 mmol) instead of dGMP and ACVDP tributylammonium salt (194 mg, 0.28 mmol), to give ACVTP-T sodium salt as yellow powder (100 mg, 0.13 mmol, yield=46%).

$^1$H-NMR (D$_2$O, pH 7.5, 200 MHz) δ (ppm): 1.95 (s, 3H), 2.31-2.40 (m, 1H), 3.83-3.89 (m, 2H), 4.12-4.29 (m, 5H), 4.61-4.68 (m, 1H), 5.59 (s, 1H), 6.31-6.38 (t, J=6.59, 1H), 7.66 (s, 1H), 7.79 (s, 1H).

$^{31}$P-NMR (D$_2$O, pH 7.5, 80 MHz) δ (ppm): −11.30:−11.64 (d, J=19.50), −11.59:−11.83 (d, J=19.50), −23.32:−23.80 (t, J=19.50).

EXAMPLE 6

Preparation of 3'-azidothymidine-5'-monophosphate

A mixture of 100 mg of 3'-azido-thymidine (0.37 mmol) and 0.5 ml triethylphosphate was gradually added to a mixture of 1 ml triethylphosphate and 100 μl phosphorus oxychloride (1.0 mmol) at 0° C. The mixture was maintained at 0-4° C. for 16 h under stirring. Then 10 ml of ice-cold 5% NaHCO$_3$ in water was added and after stirring at 0° C. for 1 hour, the pH was adjusted to 7.0 with NaOH 1M. After further 12 h under stirring, the mixture was extract with 3×10 ml of diethyl ether to remove triethylphosphate. The water solution was subjected to volume reduction (1 ml) and loaded onto a DEAE-cellulose column. The column was eluted with a linear gradient (0.05-0.4 M) of triethylammonium bicarbonate, pH 7.5. Appropriate fractions were evaporated under vacuum. Methanol was added and evaporated again to remove triethylammonium bicarbonate obtaining 3'-azidothymidine-5'-monophosphate triethylammonium salt as white solid (90 mg, 0.15 mmol, yield=40%).

$^1$H-NMR (D$_2$O, pH 7.5, 200 MHz) δ (ppm): 1.23-1.30 (t, J=7.32, 18H), 1.92 (s, 3H), 2.44-2.52 (m, 2H), 3.13-3.24 (q, J=7.32, 12H), 3.96-4.00 (m, 2H), 4.12-4.20 (m, 1H), 4.46-4.54 (m, 1H), 6.22-6.29 (t, J=6.59, 1H), 7.81 (s, 1H).

$^{31}$P-NMR (D$_2$O, pH 7.5, 80 MHz) δ (ppm): 2.57 (s).

EXAMPLE 7

Preparation of 2',3'-dideoxycytidine-5'-monophosphate

The procedure described above in Example 6 for the synthesis of 3'-azidothymidine-5'-monophosphate was followed for the preparation of 2'3'-dideoxycytidine-5'-monophosphate, using 2'3'-dideoxycytidine (ddC, 100 mg, 0.47 mmol) instead of AZT, to give 2'3'-dideoxycytidine-5'-monophosphate as white solid (ddCMP, 145 mg, 0.28 mmol, yield=59%).

$^1$H-NMR (D$_2$O, pH 7.5, 200 MHz) δ (ppm): 1.23-1.30 (t, J=7.32, 18H), 1.74-2.11 (m, 2H), 2.24-2.40 (m, 2H), 3.13-3.24 (q, J=7.32, 12H), 3.85-3.90 (m, 1H), 4.02-4.11 (m, 1H), 4.18-4.30 (m, 1H), 5.88-5.92 (m, 1H), 6.04-6.08 (d, J=7.32, 1H), 8.08-8.12 (d, J=7.32, 1H).

$^{31}$P-NMR (D$_2$O, pH 7.5, 80 MHz) δ (ppm): 1.30 (s).

EXAMPLE 8

Preparation of 2',3'-dideoxycytidine-5'-diphosphate

The procedure described above in Example 3 was followed for the preparation of 2',3'-dideoxycytidine-5'-diphosphate (ddCDP) using 2'3'-dideoxycytidine-5'-monophosphate triethylammonium salt (105 mg, 0.2 mmol) instead of acycloguanosine monophosphate, to give ddCDP as white solid (100 mg, 0.14 mmol, yield=70%).

$^1$H-NMR (D$_2$O, pH 7.5, 200 MHz) δ (ppm): 1.23-1.30 (t, J=7.32, 18H), 1.62-1.96 (m, 2H), 2.12-2.37 (m, 2H), 3.13-3.24 (q, J=7.32, 12H), 3.75-3.80 (m, 1H), 3.92-4.02 (m, 1H), 4.11-4.21 (m, 1H), 5.85-5.88 (m, 2H), 7.81-7.85 (d, J=7.32, 1H).

$^{31}$P-NMR (D$_2$O, pH 7.5, 80 MHz) δ (ppm): −4.51:−6.47 (br s), −8.40:−9.40 (br s).

EXAMPLE 9

Preparation of Acycloguanosyl-3'-azidothymidine-5'-triphosphate

The procedure described above in Example 3 was followed for the preparation of ACV-TP-AZT using 3'-azidothymidine-5'-monophosphate triethyammonium salt (AZTMP, 90 mg, 0.16 mmol) instead of dGMP and ACVDP tributylammonium salt (80 mg, 0.12 mmol), to give ACV-TP-AZT sodium salt as yellow powder (30 mg, 0.04 mmol, yield=33%).

$^1$H-NMR (D$_2$O, pH 7.5, 200 MHz) δ (ppm): 1.91 (s, 3H), 2.36-2.52 (m, 2H), 3.72-3.83 (m, 2H), 4.05-4.24 (m, 4H), 4.52-4.63 (m, 1H), 5.43 (s, 2H), 6.22-6.31 (t, J=7.32, 1H), 7.75 (s, 1H), 7.88 (s, 1H).

$^{31}$P-NMR (D$_2$O, pH 7.5, 80 MHz) δ (ppm): −11.38:−11.63 (d, J=18.30), −11.77:−12.01 (d, J=18.31), −23.11:−23.56 (t, J=18.31).

EXAMPLE 10

Preparation of 2',3'-dideoxycytidine-2'-deoxy-5'-guanosyltriphosphate

The procedure described above in Example 3 was followed for the preparation of ddC-TP-dG using 2',3'-dideoxycytidine-5'-diphosphate triethylammonium salt (ddCDP, 100 mg, 0.14 mmol) instead of ACVDP triethylammonium salt, and 2'deoxyguanosine-5'-monophosphate disodium salt (dGMP, 98 mg, 0.28 mmol), to give ddC-TP-dG sodium salt as yellow powder (20 mg, 0.04 mmol, yield=28%).

$^1$H-NMR (D$_2$O, pH 7.5, 200 MHz) δ (ppm): 1.74-2.11 (m, 2H), 2.35-2.75 (m, 4H), 3.70-3.85 (m, 2H), 3.92-4.02 (m, 1H), 4.11-4.21 (m, 2H), 4.52-4.63 (m, 1H), 5.50 (s, 2H), 6.06-6.27 (m, 2H), 7.83-785 (d, J=7.30, 1H), 7.95 (s, 1H).

$^{31}$P-NMR (D$_2$O, pH 7.5, 80 MHz) δ (ppm): −11.13:−11.36 (d, J=18.31, 2P), −22.52:−22.99 (t, J=18.31).

The invention claimed is:

1. A compound having general formula (I)

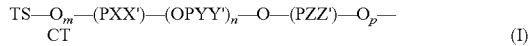
(I)

wherein

TS is a substituent wherein an included hydroxyl substituent of TS—OH has been removed to produce said TS substituent and wherein TS—OH is selected from the group consisting of 2-amino-9-[(2R,4S,5R)-3-hydroxy-5-(hydroxymethyl)oxolan-2-yl]-3H-purin-6-one, 2'-deoxy-5'-adenylic acid, 1-(2-deoxy-β-D-erythro-pentofuranosyl)-5-methyl-2,4-(1H,3H)-pyrimidinedione, 1-[(2R,4S,5S)-4-azido-5-(hydroxymethyl)-oxolan-2-yl]-5-methyl-1,2,3,4-tetrahydropyrimidine-2,4-dione, 2'-deoxyguanosine, 2'-deoxyadenosine 7-deaza-2'-deoxyguanosine, 7-deaza-2'-deoxyadenosine, 6-thio-2'-deoxyguanosine, 2',3'-dideoxyguanosine, 2',3'-dideoxyinosine, 3'-azido-3'-deoxythymidine, carbovir, adefovir, and tenofovir, CT is a substituent wherein an included hydroxyl substituent of CT-OH has been removed to produce said CT substituent and wherein CT-OH is selected from the group consisting of acyclovir, penciclovir, ganciclovir, 7-methyl-guanosine, gemcitabine, fluorodeoxyuridine, fluorouridine, fludarabine, 2-chloro-2'deoxyadenosine, idoxuridine, cytarabine, triciribine, 5-aza-2'-deoxycytidine, 2',3'-dideoxy-2',3'-didehydrouridine, 2',3'-dideoxyuridine, 5-hydroxy-2'-deoxycytidine, 3-deazauridine, enocitabine, 2',3'-dideoxycytidine, lamivudine, emtricitabine, (S)-1-(3-hydroxy-1-methoxypropyl)cytosine, (−)-2'-deoxy-3'-oxa-4'-thiocytidine, racivir, reverset, 1-(1,3-dihydroxy-2-propoxy-methyl)cytosine, (2'S)-2'-deoxy-2'-C-methylcytidine, 1-(2-deoxy-2-methylene-β-D-erythro-pentofuranosyl)cytosine, 1-(2-C-cyano-2-deoxy-1-β-D-arabino-pentofuranosyl)cytosine, 1-(3-C-ethynyl-β-D-ribo-pentofuranosyl)cytosine, β-L-1-(5-hydroxymethyl-1,3-dioxolan-2-yl) cytosine, and (E)-2'-deoxy-2'-(fluoromethylene)cytidine, X, Y, and Z are selected from the group consisting of O and S, X', Y' and Z' are selected from the group consisting of O, CT', O—CT', R and OR, wherein CT' is a substituent equal to or different from CT wherein CT' and CT are both selected from the alternatives encompassed by the above definition of CT, and R is selected from the group consisting of alkyl, lower alkyl, aryl and aryl alkyl, m=0 or 1, n=1 or 2, and p=0 or 1.

2. The compound according to claim 1, wherein X=X'=Z=Z'=O and m=1.

3. The compound according to claim 1, wherein said TS is the residue of a nucleoside selected from the group consisting of 2-amino-9-[(2R,4S,5R)-3-hydroxy-5-(hydroxymethyl)oxolan-2-yl]-3H-purin-6-one, 2'-deoxy-5'-adenylic acid, 1-(2-deoxy-β-D-erythro-pentofuranosyl)-5-methyl-2,4-(1H,3H)-pyrimidinedione, 7-deaza-2'-deoxyguanosine, 7-deaza-2'-deoxyadenosine, 6-thio-2'-deoxyguanosine, 2',3'-dideoxyguanosine, 2',3'-dideoxyinosine, 1-[(2R,4S,5S)-4-azido-5-(hydroxymethyl)-oxolan-2-yl]-5-methyl-1,2,3,4-tetrahydropyrimidine-2,4-dione, carbovir, adefovir and tenofovir.

4. The compound according to claim 1, wherein R is selected from methyl and phenyl.

5. The compound according to claim 4, wherein R is phenyl.

6. The compound according to claim 1, selected from the group consisting of α-(acycloguanosyl)γ-(2'-deoxyguanosin-5'-yl) triphosphate (ACVTPdG), acycloguanosyl 2'-deoxy-5'-adenosyltriphosphate (ACVTPdA), acycloguanosyl-5'-thymidyltriphosphate (ACVTPT), acycloguanosyl-3'-azido-3'-deoxythymidine-5'-triphosphate (ACVTPAZT), and 5'-(2',3'-dideoxycytidinyl)-2'-deoxy-5-guanosyltriphosphate (ddCTPdG).

7. The compound of claim 1, wherein the alkyl R group is selected from lower alkyl, aryl, and aryl alkyl.

8. A composition comprising a compound as defined in claim 1 and one or more pharmaceutically acceptable excipient(s) and/or diluents(s), in association with one or more adjuvants.

* * * * *